United States Patent [19]

Aoshiro et al.

[11] Patent Number: 4,771,766

[45] Date of Patent: Sep. 20, 1988

[54] GUIDE TUBE ASSEMBLY OF ENDOSCOPE

[75] Inventors: Hisatake Aoshiro, Misato; Mitsuru Sato, Tokyo, both of Japan

[73] Assignee: Kabushiki Kaisha Machida Seisakusho, Tokyo, Japan

[21] Appl. No.: 64,224

[22] Filed: Jun. 19, 1987

[30] Foreign Application Priority Data

Jul. 8, 1986 [JP] Japan .................................. 61-158843
Aug. 25, 1986 [JP] Japan .................................. 61-197393

[51] Int. Cl.$^4$ .............................................. A61B 1/12
[52] U.S. Cl. ..................................................... 128/4
[58] Field of Search ........................... 128/3, 4, 5, 6, 7; 604/317, 319, 321

[56] References Cited

U.S. PATENT DOCUMENTS

| | | | |
|---|---|---|---|
| 3,960,143 | 6/1976 | Terada | 128/4 |
| 4,111,204 | 9/1978 | Hessel | 604/321 |
| 4,261,343 | 4/1981 | Ouchi et al. | 128/4 |
| 4,333,480 | 6/1982 | Villari et al. | 604/317 X |
| 4,589,403 | 5/1986 | Ouchi et al. | 128/4 |

OTHER PUBLICATIONS

Gore-Tex® Expanded PTFE, W. L. Gore & Associates, Inc., Elkton, Md., 8 page brochure, ©1980.

Primary Examiner—William H. Grieb
Attorney, Agent, or Firm—Kane, Dalsimer, Sullivan, Kurucz, Levy, Eisele and Richard

[57] ABSTRACT

An endoscope comprising a proximal structure and an inserting structure extending from an operating body of the proximal structure. A guide tube assembly extending within the inserting structure comprises an inner tube formed of porous resin and an outer tube formed of imperforate resin. The inner tube has one end communicating with a proximal opening provided in the proximal structure and the other end communicating with a distal opening provided in a distal end of the inserting structure. A hollow portion of the inner tube communicates with an annular region between the inner and outer tubes through pores of a peripheral wall of the inner tube. The annular region communicates with a port provided in at least one of the proximal structure and the distal end of the inserting structure. Fluid such as, for example, disinfecting fluid can be supplied from the port or can be discharged from the port, and can flow between the hollow portion of the inner tube and the annular region between the inner and outer tubes through the pores.

24 Claims, 4 Drawing Sheets

GUIDE TUBE ASSEMBLY OF ENDOSCOPE

BACKGROUND OF THE INVENTION

The present invention relates generally to endoscopes and, more particularly, to a guide tube assembly of an endoscope, for guiding an elongated operating instrument or the like, for example.

A usual or general endoscope comprises an operating body and a flexible inserting portion extending therefrom. The inserting portion has a distal end section serving as a yieldable or bendable section which can be curved by remote-operation at the operating body. A distal end of the bendable section is formed into a relatively hard tip component. Received within the inserting portion is a guide tube for guiding an elongated operating instrument or the like. The operating instrument is inserted from a proximal opening provided in the operating body, passes through the guide tube, and is led in a body cavity or coelom through a distal opening provided in the tip component, so that the operating instrument can tear off some tissues from the inner wall of the body cavity, for example.

The guide tube is required to have low coefficient of friction, in order to permit the operating instrument to be smoothly inserted and withdrawn. In addition, the guide tube is required to have low bending resistance, in order to facilitate the bending operation of the bendable section. Moreover, the guide tube is also required to be curved in a round fashion when the bendable section is bent, such that the cross-sectional shape of the guide tube is maintained substantially circular at the curved region. The reason for this is that, should the guide tube be folded in an acute angle and the cross-sectional shape thereof be crushed, it would become impossible to guide the operating instrument.

Drawn, porous tetrafluoroethylene resin is often used as a material of the guide tube which satisfies the above requirements.

Since the guide tube formed of the porous tetrafluoroethylene resin has repellency, usual water having high surface tension cannot pass through the minute or fine pores of the peripheral wall of the guide tube. However, humor or the like having low surface tension can be permeated into the pores. For this reason, measures are taken to apply fluoro rubber to an inner or an outer peripheral surface of the guide tube so as to partially impregnate the peripheral wall thereof with the fluoro rubber, to thereby prevent the humor from leaking through the pores, as has been proposed in, for example, Japanese Utility Model Laid-Open Application Nos. 54-115184 and 54-115185.

With the construction described above, however, the bending resistance of the guide tube increases, because the peripheral wall thereof is impregnated with the rubber such that the coating is integrally formed on the inner or outer peripheral surface. This reduces the advantage of the porous tetrafluoroethylene resin.

In particular, if the outer peripheral surface of the guide tube is coated with the rubber, bacterial tend to propagate within the pores, because the humor penetrates into the pores until it reaches the rubber coating. For this reason, it is necessary to sterilize or disinfect the guide tube after use of the endoscope. However, the conventional construction has the following problems.

The case where disinfecting liquid is employed will first be described in detail. As the disinfecting liquid passes through the guide tube, the disinfecting liquid is permeated into the pores of the peripheral wall of the guide tube. However, the pores are closed at their respective outer ends by the rubber coating and, therefore, the disinfecting liquid cannot reach the bottoms of the respective pores. This makes it difficult to effect sufficient or complete disinfection. Moreover, after the disinfection, the inner tube is rinsed with water and is dried, but sufficient drying cannot be effected because the outer ends of the respective pores are closed. The fluid remains at the bottoms of the respective pores. Thus, bacterial might again propagate.

In case of employment of disinfecting gas, the endoscope is first washed with usual water. However, since the pores are closed at their respective outer ends, no sufficient water reaches the bottoms of the respective pores so that the washing cannot be effected in a reliable manner. In addition, after the washing, the endoscope is disposed within a chamber which is under vacuum, to remove air and water from the interior of the endoscope. Subsequently, the endoscope is disinfected with the disinfecting gas. However, since a part of the liquid such as humor, washing water and the like remains at the bottoms of the respective pores, it is not possible to achieve sufficient sterilization due to the disinfecting gas.

Japanese Utility Model Laid-Open Application Nos. 52-90990 and 57-7502 disclose a guide tube assembly of double tube structure. The inner tube of the former application is formed by a helically wound metallic wire, but is not formed of porous resin as is in the present invention. The inner tube of the latter application is formed of porous resin, but the inner and outer tubes do not define therebetween an annular region or space through which fluid can flow.

OBJECT AND SUMMARY OF THE INVENTION

It is an object of the invention to provide an endoscope comprising a guide tube assembly having an inner and an outer tube, in which it is possible to disinfect and wash the inner tube in a reliable and positive manner.

According to the invention, there is provided an endoscope comprising:
  a proximal structure including at least an operating body and provided with at least one proximal opening;
  an elongated inserting structure extending from the operating body and having a distal end provided with at least one distal opening;
  a guide tube assembly extending through the inserting structure and comprising an inner tube formed of porous resin and having one end thereof communicating with the proximal opening and the other end communicating with the distal opening, and an outer tube formed of imperforate resin and surrounding the inner tube, the inner tube having a hollow portion communicating with an annular region between the inner and outer tubes through pores of a peripheral wall of the inner tube; and
  port means provided in at least one of the proximal structure and the distal end of the inserting structure, a fluid being capable of passing through the port means, the port means communicating with the annular region between the inner and outer tubes.

DETAILED DESCRIPTION

Figures 1, 2:
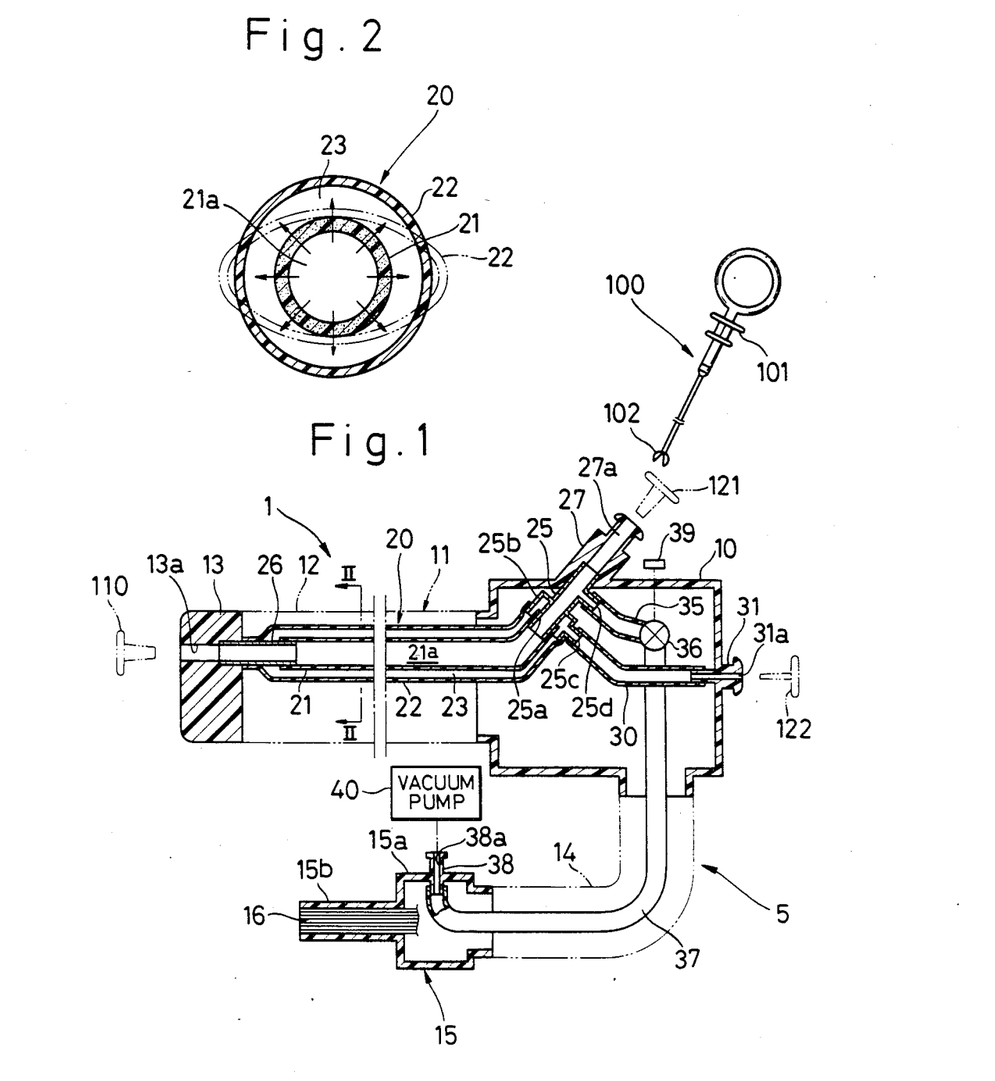
FIG. 1 is a cross-sectional view showing an endoscope according to a first embodiment of the invention.
FIG. 2 is an enlarged cross-sectional view taken along line II—II in FIG. 1.

Referring first to FIGS. 1 and 2, there is illustrated an endoscope, generally designated by the reference numeral 1, according to a first embodiment of the invention. The endoscope 1 comprises a proximal structure 5 which, in the illustrated embodiment, includes an operating body 10 and a connector 15 connected thereto through a flexible guide tube 14. The endoscope 1 also comprises an elongated flexible inserting structure 11 extending from the operating body 10 and adapted to be inserted into a body cavity or coelom. The inserting structure 11 has a distal end portion serving as a yieldable or bendable section 12 which can be curved by remote-operation at the operating body 10 in a known manner. The distal end of the bendable section 12 is formed into a relatively hard tip component 13.

The connector 15 comprises a hollow body 15a and an elongated tubular portion 15b extending therefrom. A bundle of optical fibers 16 for transmitting illuminating light has one end which is received in the tubular portion 15b. The bundle of optical fibers 16 extends through the guide tube 14, the operating body 10 and the inserting structure 11. The other end of the bundle of optical fibers 16 reaches the tip component 13 and faces an illuminating window, not shown, formed in the tip component 13. As the connector 15 is fitted in a receptacle of a light source, not shown, light from the light source is supplied to the one end face of the bundle of optical fibers 16, is transmitted therethrough, and is irradiated into the body cavity through the illuminating window.

Figure 3:
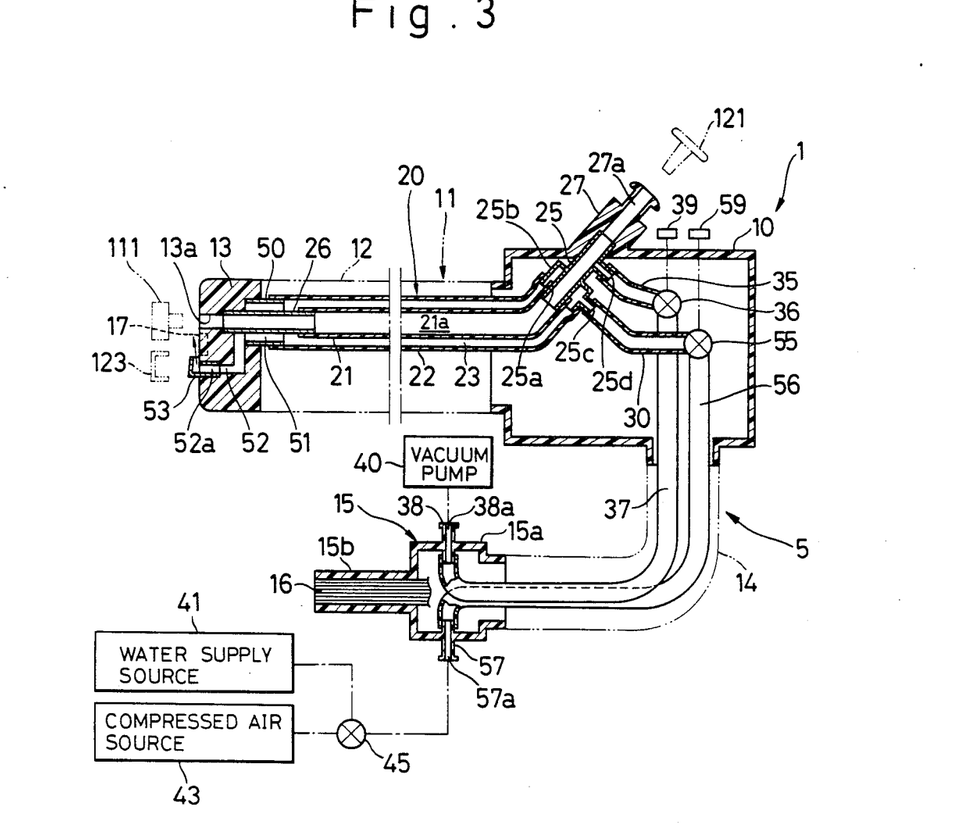
FIG. 3 is a view similar to FIG. 1, but showing a second embodiment of the invention.

The tip component 13 is formed with a viewing window like that designated by the reference numeral 17 in FIG. 3, in addition to the illuminating window. The viewing window is optically connected to a solid-state image pickup element, not shown, through an objective optical system, not shown. Electric wires having their respective one ends thereof connected to the solid-state image pickup element extend through the inserting structure 11, the operating body 10 and the guide tube 14. The respective other ends of the electric wires are led to the outside through the side wall of the hollow body 15a of the connector 15, and are connected to a signal processor. The signal processor processes picture signals from the solid-state image pickup element, and sends television signals to a monitor television, so that an operator can view the image of the body cavity obtained by the solid-state image pickup element. An ocular system may be provided at the operating body 10 so that the image entering through the viewing window and transmitted to the operating body 10 through an optical image transmitting system can be viewed at the ocular system.

A guide tube assembly 20, by which the present invention is characterized, is received in and extends within the inserting structure 11. The guide tube assembly 20 comprises an inner tube 21 and an outer tube 22 surrounding the same in concentric relation. The inner tube 21 is formed of porous resin such as, for example, drawn polytetrafluoroethylene, and minute or fine pores are formed through a peripheral wall of the inner tube 21. The outer tube 22 is formed of usual imperforate resin. The inner and outer tubes 21 and 22 define therebetween an annular gap or space which communicates with a hollow portion 21a of the inner tube 21 through the pores of the peripheral wall thereof. The annular space serves as an annular fluid passage 23 for washing fluid and disinfecting fluid, subsequently to be described.

One ends of the respective inner and outer tubes 21 and 22 are connected to the operating body 10 through a metallic pipe 25, and the respective other ends are connected to the tip component 13 through a metallic tube 26.

Specifically, a tubular connecting projection 27 extends outwardly from the wall of the operating body 10 in an integral manner. The connecting projection 27 is formed with a through bore 27a having an outer open end serving as a proximal opening. One end of the above-mentioned metallic pipe 25 is fixedly fitted in an inner end of the through bore 27a. The other end of the metallic pipe 25 is formed into a double pipe structure having an inner pipe section 25a and an outer pipe section 25b. The one end of the inner tube 21 is connected to the inner pipe section 25a, and the one end of the outer tube 22 is connected to the outer pipe section 25b. The tip component 13 is formed with a through bore 13a having an outer open end serving as a distal opening. A metallic pipe 26 has one end thereof which is fixedly fitted in an inner end of the through bore 13a. The other end of the metallic pipe 26 is connected to the other end of the inner tube 21. The other end of the outer tube 22 is connected to the outer peripheral surface of an intermediate portion of the metallic pipe 26.

The respective connecting end portions of the inner tube 21 to the metallic pipes 25 and 26 are formed so as to have no pores. Alternatively, rubber is applied to inner and outer peripheral surfaces of each of the respective connecting end portions of the inner tube 21 such that the respective connecting end portions are partially impregnated with rubber. Thus, the pores of the respective connecting end portions are closed. The reason for doing so is that flow of fluid such as disinfecting fluid through pores subsequently to be described in detail cannot be expected at the connecting end portions.

A tubular connecting projection 25c is formed on the outer pipe section 25b of the metallic pipe 25. A connecting tube 30 has one end thereof connected to the connecting projection 25c. The other end of the connecting tube 30 is connected to a connecting projection 31 formed on the wall of the operating body 10. The connecting projection 31 is formed with a through bore 31a serving as a port through which fluid can pass.

A tubular connecting projection 25d is formed on an intermediate portion of the metallic pipe 25. A connecting tube 35 has one end thereof connected to the connecting projection 25d and the other end to which one end of a suction tube 37 is connected through a valve 36. The suction tube 37 extends within the guide tube 14 and reaches the connector 15. The other end of the suction tube 37 is connected to a tubular connecting projection 38 formed on the wall of the hollow body 15a. The connecting projection 38 is provided with a through bore 38a having an outer open end which serves as a proximal opening. The through bore 38a is connected to a vacuum source or vacuum pump 40. The valve 36 is adapted to be opened and closed by an operating button 39 arranged on the operating body 10.

In the endoscope constructed as described above, the inserting structure 11 is inserted into the body cavity to view the interior thereof. Specifically, an elongated operating instrumen 100 is inserted into the inner tube 21 of the guide tube assembly 20 through the bore 27a and is projected into the body cavity from the bore 13a. The operating instrument 100 is well known and will not therefore be described in detail. The illustrated operating instrument 100 comprises an operating portion 101 and a pair of generally semi-spherical tearing blades 102 which are opened ad closed by remote-operation at the operating portion 101, to collect tissues of the body cavity. After collection, the operating instrument 100 is withdrawn out of the endoscope 1. The operating instrument 100 can smoothly be inserted into and withdrawn from the endoscope 1, because the inner tube 21 is formed of porous tetrafluoroethylene resin so that the inner peripheral surface of the inner tube 21 is very low in coefficient of friction. The operating instrument 100 should not be limited to the illustrated one, but may be ones having various functions other than the tissue collection.

When the bendable section 12 is curved by the remote-operation at the operating body 10, the inner tube 21 is also bent or curved. However, the bending resistance of the inner tube 21 is low, because the pores located inwardly of the curved region are crushed. Further, the inner tube 21 is curved in a round fashion, and the cross-sectional shape of the inner tube 21 is maintained substantially circular at the curved region. Accordingly, it is possible to effect, in a reliable manner, guiding of the operating instrument 100 and drawing or suction of liquid subsequently to be described.

Furthermore, when curved, the outer tube 22 is supported by the inner tube 21 and therefore is not folded in an acute angle, is indicated by the two-dot-and-dash lines. This makes it possible to reduce the wall thickness of the outer tube 22, enabling the bending resistance thereof to be reduced. Since both the tubes 21 and 22 are low in bending resstance and they are not integral with each other, the resultant bending resistance of the guide tube assembly 20 is low, making it possible to easily perform the bending or curving operation of the bendable section 12.

When it is desired to remove humor out of the body cavity, the bore 27a is closed by a rubber plug 121 and the bore 31a is closed by a rubber plug 122. Subsequently, the perating button 39 is depressed to open the valve 36. Humor is drawn through the bore 13a by the vacuum pump 40, is caused to flow through the hollow portion 21a of the inner tube 21, the connecting tube 35 and the suction tube 37, and is discharged from the bore 38a.

When, as described above, the operating instrument 100 is inserted into and withdrawn from the endoscope 1 and when the humor is drawn out of the body cavity, the humor ad/or muck adhere to the inner peripheral surface of the inner tube 21, and a part of the humor and/or muck is permeated or penetrated into the pores of the peripheral wall of the inner tube 21. Accordingly, the endoscope 1 is required to be disinfected after use.

The case where disinfecting liquid is employed to disinfect the endoscope 1 will first be described. At the outset, the bore 13a is closed by an operator's finger or a rubber plug 110, and the plugs 121 and 122 are removed respectively from the bores 27a and 31a. The operating button 39 is maintined not depressed to close the valve 36. The hollow potion 21a of the inner tube 21 communicates with the outside only through the bore 27a at the one end of the inner tube 21. Thus, a flow passageway for the disinfecting liquid is formed, which extends from the bore 27a to the bore 31a through the hollow portion 21a of the inner tube 21, the pores of the peripheral wall of the inner tube 21, the fluid passage 23 and the connecting pipe 30. Pressurized disinfecting liquid is supplied from the bore 27a. The supplied disinfecting liquid is first filled in the hollow portion 21a. Because of the pressurization, the disinfecting liquid is caused to pass through the pores, and to flow into the fluid passage 23. Since the disinfectng liquid is caused to pass through the pores, the inner tube 21 can reliably or positively be disinfected. In the course of passage of the disinfecting liquid through the pores, the humor and/or muck staying in the pores is caused to flow out thereof together with the disinfecting liquid. The disinfecting liquid entering the flow passage 23 is caused to flow through the connecting tube 30 and is dicharged through the bore 31a.

Another flow passageway for the disinfecting liquid can be employed in substitution for the above-mentioned flow passageway. That is, the plugs 121, 122 and 110 are removed respectively from the bores 27a, 31a and 13a, and the valve 36 is closed. Thus, the another flow passageway is formed, which includes the hollow portion 21a and the fluid passage 23, and which has a first end communicating with the bore 31a, a second end communicating with the bore 27a and a third end communicating with the bore 13a. Pressurized disinfecting liquid is supplied from the bore 31a. The supplied disinfecting liquid is first filled in the fluid passage 23. The disinfecting liquid is caused to pass through the pores and to flow into the hollow portion 21a and, subsequently, is discharged through the bores 13a and 27a.

Still anther flow passageway for the disinfecting liquid can be employed. That is, the bores 13a and 27a are closed respectively by the plugs 121 and 110, and the plug 122 is removed from the bore 31a. The operating button 39 is depressed to open the valve 36. Thus, the still another flow passageway is formed, which extends from the bore 31a to the bore 38a through the connecting tube 30, the fluid passage 23, the pores, the hollow portion 21a and the tubes 35 and 37. The vacuum pump 40 is actuate to apply negative pressure to the bore 38a. The disinfecting liquid is drawn through the bore 31a, caused to flow through the still another flow passageway, and is discharged from the bore 38a. Also in this case, the disnfecting liquid can be caused to pass through the pores of the peripheral wall of the inner tube 21.

Subsequently, washing water is likewise caused to flow through the guide tube assembly 20. At this time, the washing water can be caused to pass through the pores, making it possible to ensure that the disinfecting liquid is removed from th pores. After the washing, the guide tube assembly 20 is dried. During this drying, the washing water is easily evaporated, because the pores are open at their respective oposite ends. Thus, no such problems occur that liquid stays in the pores to permit bacteria to propagate. When drying, pressurized hot air may be caused to flow in a manner similar to the above-described manner of passing of the disinfecting liquid and the washing water, or negative pressure may be applied to a selected one of the above-described bores. In this case, the drying air is caused to forcibly pass through the pores, making it possile to ensure the drying.

The case where disinfecting gas such as ethylene oxide or the like is employed, will next be described. At the outset, washing water is caused to flow through the guide tube assemble 20 in a manner similar to that described above. Since the washing water is caused to pass through the pores of the peripheral wall of the inner tube 21, the pores can reliably be washed with the water. Subsequently, the endoscope 1 is disposed within a vacuum chamber to remove ir and water out of the interior of the endoscope 1. At this time, since the pores are open at opposite ends, liquid can reliably be removed out of the pores. Subsequently, the aforesaid chamber is brought to disinfecting gas atmosphere, to perform disinfection. Since the pores are open at the opposite ends, the disinfection gas can sufficiently be spread into the pores. Moreover, since no liquid remains in the pores as described above, the disinfection can be effected reliably. Positive or negative pressure may be employed like the above-described disinfecting liquid, to cause the disinfecting gas to forcibly pass through the pores, making it possible to further ensure the disinfection.

Figure 4:
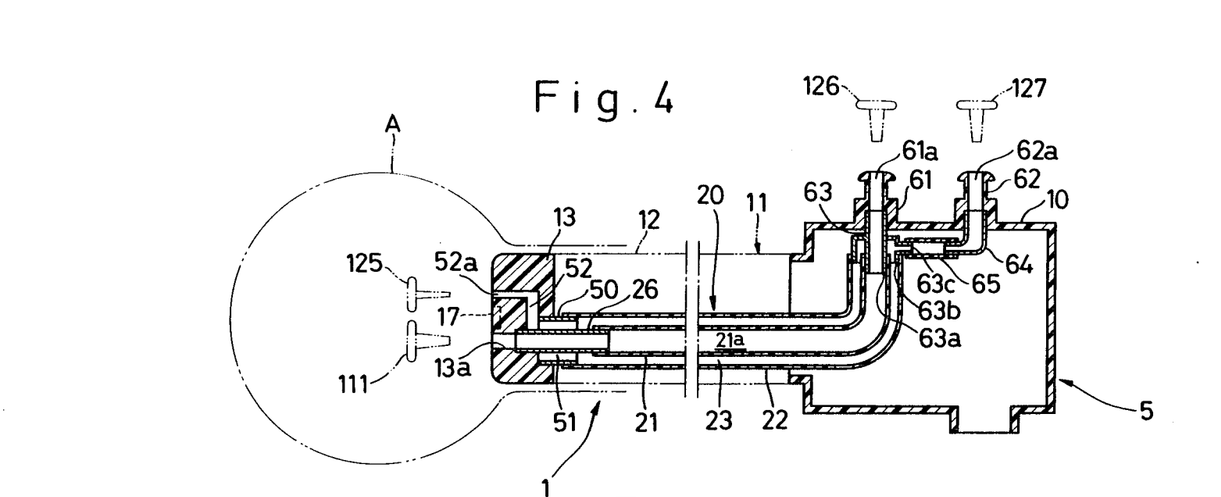
FIG. 4 is a view similar to FIG. 1, but showing a third embodiment of the invention.
Figure 5:
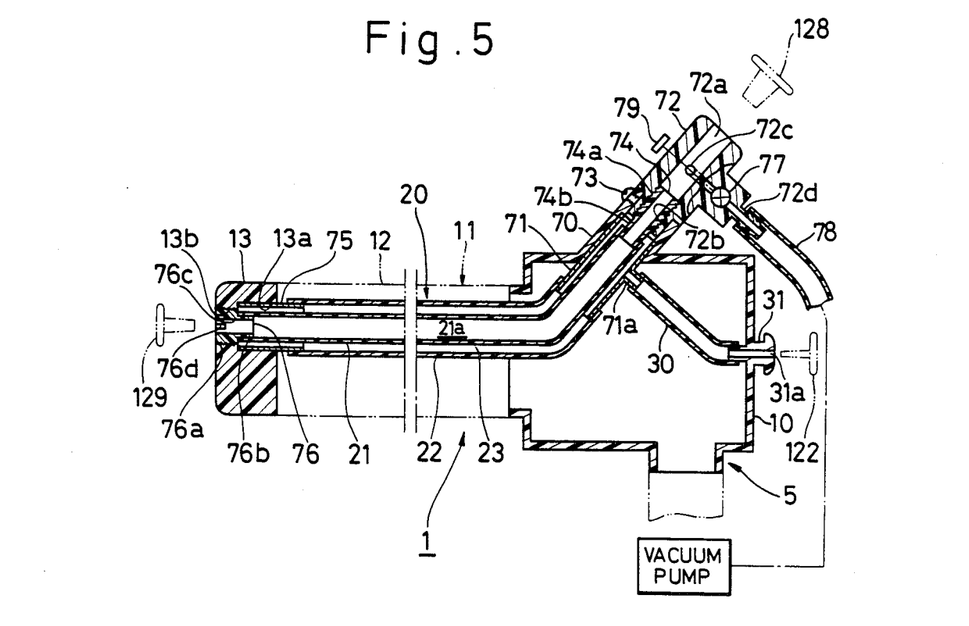
FIG. 5 is a view similar to FIG. 1, but showing a fourth embodiment of the invention.

FIGS. 3, 4 and 5 illustrate a second, a third and a fourth embodiment of the invention, respectively. In FIGS. 3 through 5, like reference numerals are used to designate parts or components like or similar to those illustrated in FIGS. 1 and 2, and the description of such like or similar parts or components will therefore be omitted to avoid duplication.

In the second embodiment shown in FIG. 3, the fluid passage 23 serves also as a water supply and compressed-air supply passage through which water for washing the viewing window 17 and compressed air for drying the same flow. Since no separate tube forming the water supply and compressed-air supply passage is required, it is possible to reduce the diameter of the inserting structure 11. Specifically, the metallic pipe 26 and a larger diameter metallic pipe 50 concentric thereto are fixedly secured to the tip component 13. The end of the outer tube 22 is connected to the metallic pipe 50. The annular fluid passage 23 formed between the inner and outer tubes 21 and 22 communicates with the outside through an annular passage 51 defined between the pipes 26 and 50, a passage 52 formed in the tip component 13, and a nozzle 53 fitted in an outer open end 52a of the passage 52. The nozzle 53 is directed toward the viewing window 17. The outer open end 52a serves as a port through which fluid can pass. A water delivery tube 56 has one end connected, through a valve 55, to the connecting tube 30 connected to the metallic pipe 25. The valve 55 is adapted to be opened and closed by an operating button 59. The tube 56 extends within the guide tube 14 and has the other end connected to a connecting projection 57 which is provided on the wall of the hollow body 15a of the connector 15. The connecting projection 57 is formed with a through bore 57a having an outer open end which serves as a port and which is connected to a water supply source or pump 41 and a compressed air source or compressor 43 through a selector valve 45.

In the second embodiment constructed as described above, the insertion and withdrawal of the operating instrument like that designated by the reference numeral 100 in FIG. 1, and the drawing operation by the vacuum pump 40 are performed in a manner similar to that of the above-described first embodiment. When the viewing window 17 is contaminated with humor or the like, the operating button 59 is depressed to open the valve 55, and the selector valve 45 is changed over to permit the water supply source 41 to communicate with the bore 57a, to thereby supply water from the source 41 to the bore 57a. The supplied water flows through the tubes 56 and 30 and through the fluid passage 23 and the passages 51 and 52, and is injected from the nozzle 53 toward the viewing window 17 to wash the same. Subsequently, the selector valve 45 is changed over to permit the compressed air source 45 to communicate with tne bore 57a, to thereby inject the compressed air from the nozzle 53 toward the viewing window 17 to remove the washing water therefrom.

In the second embodiment illustrated in FIG. 3, a flow passageway for disinfecting fluid is formed. That is, the valves 36 and 55 are closed, the bore 13a is closed by an operator's finger or a rubber plug 111. Thus, the flow passageway is formed, which includes the hollow portion 21a and the annular passage 23 and which has one end communicating with the bore 27a and the other end communicating with the nozzle 53. Pressurized disinfecting liquid is supplied from the bore 27a. The supplied disinfecting liquid is first filled in the hollow portion 21a, is then caused to pass through the pores of the peripheral wall of the inner tube 21, is caused to flow through the fluid passage 23 and the passages 51 and 52, and is discharged from the nozzle 53.

Another flow passageway for the disinfecting liquid can be employed. That is, the bore 27a is closed by the plug 121, the plug 111 is removed from the bore 13a, and the valves 36 and 55 are closed. Thus, the another flow passageway is formed, which extends from the bore 13a to the nozzle 53 through the hollow portion 21a, the pores, the fluid passage 23 and the passages 51 and 52. Pressurized disinfecting liquid is supplied from the bore 13a, is caused to flow through the another flow passageway, and is discharged from the nozzle 53.

Still another flow passageway for the disinfecting liquid can be employed. That is, the valve 36 is closed, the valve 55 is opened, the plugs 121 and 111 are removed respectively from the bores 27a and 13a, and the nozzle 53 is closed by a rubber plug 123. Thus, the still another flow passageway is formed, which extends from the bore 57a to the bores 27a and 13a through the tubes 56 and 30, the fluid passage 23, the pores and the hollow portion 21a. In these cases, the disinfecting liquid is caused to flow from the fluid passage 23 to the hollow portion 21a through the pores, and is discharged from the bores 27a and 13a.

It is needless to say that the washing and disinfection similar to those described in connection with the first embodiment can be performed in the second embodiment.

Although the second embodiment has been described as having the fluid passage 23 which serves also as the water supply and compressed-air supply passage, the hollow portion 21a of the inner tube 21 may be employed as an exclusive passage for supplying water and compressed air to wash the viewing window 17.

The third embodiment of the invention illustrated in FIG. 4 is designed to use in viewing or observation of a urinary bladder A or the like. The tip component 13 illustrated in FIG., 4 is similar in construction to that shown in FIG. 3, except that the nozzle is not provided. The operating body 10 is provided with two connecting projections 61 and 62 which are formed with through bores 61a and 62a, respectively. The bore 61a has an outer open end serving as a proximal opening, and the bore 62a has an outer open end serving as a port. Metallic pipes 63 and 64 are fitted respectively in inner open ends of the respective bores 61a and 62a. The metallic pipe 63 has an inner end formed into a double pipe structure having inner and outer pipe sections 63a and 63b. The inner and outer tubes 21 and 22 of the guide tube assembly 20 are connected to the inner and outer pipe sections 63a and 63b, respectively. The outer pipe section 63b is formed with a connecting projection 63c which is connected to the metallic pipe 64 though a tube 65.

In the third embodiment illustrated in FIG. 4, when the urinary bladder A is viewed, washing water is supplied from the bore 61a formed in the connecting projection 61. The supplied washing water flows into the urinary bladder A through the hollow portion 21a of the inner tube 21. The washing water within the urinary bladder A is returnd into the bore 52a, flows through the passages 52 and 51 and the fluid passage 23, and is discharged form the bore 62a. Thus, stained humor is discharged out of the urinary bladder A, and the urinary bladder A is filled with the washing water. This makes it possible to ensure good viewing or observation.

In the above-described third embodiment, the opposite ends of the hollow portion 21a of the inner tube 21 communicate with the outside through the respective bores 61a and 13a, and the opposite ends of the fluid passage 23 communiate with the outside through the respective bores 62a and 52a. Accordingly, a flow passageway for disinfecting liquid or gas is formed, which extends from one of the bores 61a and 13a to the bores 52a and 62a through the hollow portion 21a, the pores of the peripheral wall of the inner tube 21 and the fluid passage 23. The other of the bores 61a and 13a is closed by a corresponding one of rubber plugs 126 and 111. Pressurized disinfecting liquid or gas is supplied from the one of the bores 61a and 13a, is caused to flow through the flow passageway, and is discharged from the bores 62a and 52a. In substitution for the pressurization, negative pressure may be applied to one of the bores 61a and 13a to draw disinfecting fluid through the bores 62a and 52a. Another flow passageway for disinfecting fluid may be employed, which extends from one of the bores 62a and 52a to the bores 61a and 13a through the fluid passage 23, the pores and the hollow portion 21a. The other of the bores 62a and 52a is closed by a corresponding one of rubber plugs 127 and 125. Pressurized disinfecting fluid is supplied to the one of the bores 62a and 52a, is caused to flow through the another flow passageway, and is discharged from the bores 61a and 13a. In substitution for the pressurization, negative pressure my be applied to one of the bores 62a and 52a to draw disinfecting fluid through the bores 61a and 13a.

The fourth embodiment illustrated in FIG. 5 is designed such that the inner tube 21 is removable or withdrawable from the endoscope 1. Specifically, a tubular connecting projection 70 having a through bore extends outwardly from the wall of the operating body 10. A metallic pipe 71 has one end fixedly fitted in an inner end of the bore of the connecting projection 70. One end of the outer tube 22 of the guide tube assembly 20 is connected to the other end of the metallic pipe 71. An attachment 72, which forms a part of the operating body 10, has a distal end which is inserted into an outer end of the bore of the connecting projection 70 and which is fixed thereto by a set scew 73. The attachment 72 is provided with a through bore 72a having an outer open end serving as a proximal opening. The bore 72a has a threaded inner end portion 72b with which a threaded outer end portion 74a of a connecting pipe 74 is threadedly engaged. One end of the inner tube 21 is connected to an inner straight end portion 74b of the connecting pipe 74.

The tip component 13 is formed with a stepped bore having an inner bore portion 13a and an outer, smaller-diameter threaded bore portion 13b extending in coaxial relation to the inner bore portion 13a. A metallic pipe 75 has one end thereof which is fixedly fitted in the inner bore portion 13a. The other end of the outer tube 22 is connected to the other end of the metallic pipe 75. An attachment 76, which forms a part of the tip component 13, has an outer threaded portion 76a which is threadedly engaged with the outer threaded bore portion 13b. The attachment 76 has an inner straight portion 76b to which the other end of the inner tube 21 is connected. The attachment 76 has a through bore 76c serving as a distal opening. An engaging groove 76d, with which a screwdriver of minus type is engageable, is formed in an outer end face of the attachment 76.

The aforementioned metallic pipe 71 is formed with a tubular connecting projection 71b which communicates with the bore 31a through the connecting tube 30.

The attachment 72 is formed therein with a suction passage 72c communicating with the bore 72a. A valve 77 is provided in the suction passage 72c and is adapted to be opened and closed by an operating button 79 arranged at the attachment 72. The suction passage 72c extends through a connecting projection 72d projecting from the attachment 72. The connecting projection 72d is connected to a suction device or vacuum pump 40 through a suction tube 78.

An operating instrument like that designated by the reference numeral 100 in FIG. 1 is inserted into the bore 72a of the attchment 72, passes through the connecting pipe 74, the hollow portion 21a of the inner tube 21 and the through bore 76c of the attachment 76, and is projected into a body cavity from the tip component 13. When humor is desired to be discharged out of the body cavity, the operating button 79 is depressed to open the valve 77. Then, the humor within the body cavity is drawn through the bore 76c by the vacuum pump 40, and is caused to flow through the hollow portion 21a, the connecting pipe 74, the suction passage 72c and the suction tube 78. In the suction of the humor, the bores 72a and 31a are closed by rubber plugs 128 and 122, respectively.

In the fourth embodiment illustrated in FIG. 5, there are two broadly divided ways of disinfection of the endoscope 1. First of the two ways is such that the inner and outer tubes 21 and 22 are simultaneously disinfected, with the inner tube 21 maintained fitted in the endoscope 1. This first disinfecting way is substantially identical with that described previously in connection with the first embodiment, and the description of the first disinfecting way will therefore be omitted to avoid duplication. The second disinfecting way is such that the inner tube 21 is withdrawn from the endoscope 1, and the inner and outer tubes 21 and 22 are disinfected separately from each other. The second disinfecting way is selected, if contamination of the inner tube 21 is violent, or there is sufficient time to spare.

The second disinfecting way will be described. At the outset, the screw 73 is loosened and, subsequently, the screwdriver is engaged with the engaging groove 76d of the attachment 76 to turn the same, to thereby move the attachment 76 inwardly, i.e., toward the metallic pipe 75 until the attachment 76 is disengaged from the threaded bore portion 13b of the tip component 13. Subsequently, the attachment 72 is pulled to withdraw the inner tube 21 out of the endoscope 1.

After the withdrawal of the inner tube 21 out of the endoscope 1, the inner tube 21 is disinfected. For example, the bore 76c of the attachment 76 is closed by a rubber plug 129, and the valve 77 is closed. Pressurized disinfecting liquid is supplied from the bore 72a of the attachment 72. The supplied disinfecting liquid is filled in the hollow portion 21a of the inner tube 21 and is caused to forcibly pass through the pores of the peripheral wall of the inner tube 21. Since the disinfecting liquid is caused to pass through the pores, the inner tube 21 is sufficiently disinfected, and the humor and/or muck staying in the pores is caused to flow out of the pores together with the disinfecting liquid. Subsequently, water is caused to flow in a manner similar to the disinfecting liquid, to wash the inner tube 21. Thereafter, the inner tube 21 is dried. In case of employment of disinfecting gas, washing water is first caused to flow through the pores. The inner tube 21 is dried and, subsequently, the disinfecting gas is caused to flow to disinfect the inner tube 21. The inner tube 21 formed of tetrafluoroethylene resin is superior in heat-resistance and pressure-resistance, and it is therefore possible to sterilize the inner tube 21 with steam of high temperature and high pressure.

The outer tube 22 is disinfected independently of the inner tube 21. For example, the bore 31a is closed by the plug 122, and pressurized disinfecting liquid is supplied through the bore of the connecting projection 70. The supplied disinfecting liquid is caused to flow through the hollow portion of the outer tube 22 and is discharged from the threaded bore portion 13b of the tip component 13. Passage of the disinfecting liquid washes away the humor and/or muck staying in the outer tube 22, so that the outer tube 22 is sufficiently disinfected.

The inner tube 21 disinfected and washed in the above-described second way is again fitted in the endoscope 1. At this time, the attachment 76 is threadedly engaged with the threaded bore portion 13b of the tip component 13 in the following manner. That is, the inner tube 21 is inserted into the outer tube 22, and the attachment 76 fixedly secured to the distal end of the inner tube 21 is positioned adjacent the threaded bore portion 13b of the tip component 13. A special jig, not shown, is prepared, which has a pair of openable and closable claws, like pliers. With the claws closed, the jig is inserted into the threaded bore portion 13b from the outside, and is inserted into the bore 76c of the attachment 76. The claws of the jig are the opened to support the attachment 76. The jig is then turned while supporting the attachment 76, to cause the same to be threadedly engaged slightly with the threaded bore portion 13b. Subsequently, the jig is withdrawn out of the threaded bore portion 13b, and the screwdriver is engaged with the engaging groove 76d of the attachment 76. The screwdriver is then turned to bring the attachment 76 into threaded engagement with the threaded bore portion 13b.

If no sufficient fruit is borne by the washing and disinfection, only the inner tube 21 may be replaced by new one.

Figure 6:
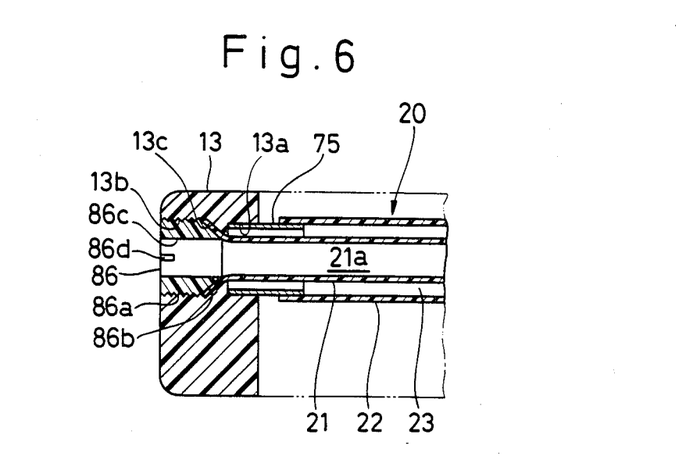
FIG. 6 is a fragmental enlarged cross-sectional views showing a modification of a distal attachment illustrated in FIG. 5.

FIG. 6 shows a modification of an attachment for attaching the inner tube 21 to the tip component 13. In the arrangement illustrated in FIG. 6, the outer tube 22 is fixedly connected to the tip component 13 through the metallic pipe 75, like the above-described fourth embodiment. A tapred bore portion 13c diverging away from the bore portion 13a is formed between the bore portions 13a and 13b.

When the inner tube 21 is attached to the tip component 13, the distal end of the inner tube 21 is previously located within the tapered bore portion 13c. It is preferable that the distal end of the inner tube 21 is tapered so as to diverge forwardly. An attachment 86 is screwed into the threaded bore portion 13b. The attachment 86 has a tapered end 86b and the other end formed with an engaging groove 86d with which a screwdriver of minus type is engageable. The attachment 86 is provided therein with a through bore 86c. As the screwdriver is engaged with the engaging groove 86d to screw the attachment 86 into the threaded bore portion 13b, the tip of the tapered end 86b is inserted into the distal end of the inner tube 21. As the attachment 86 is further advanced, the distal end of the inner tube 21 is clamped between the tapered bore portion 13c and the tapered end 86b. Thus, the distal end of the inner tube 21 is attached to the tip component 13.

Figure 7:
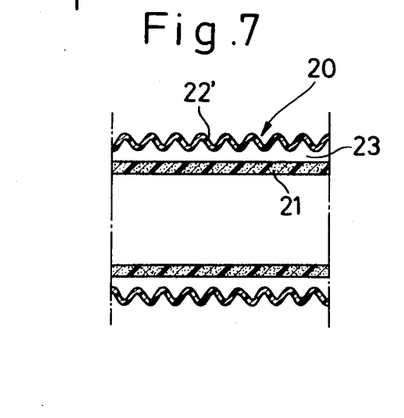
FIG. 7 is a fragmental cross-sectional view showing a modification of an outer tube.

A corrugated outer tube 22' shown in FIG. 7 may be substituted for the outer tube 21 employed in each of the above-described first through fourth embodiments. Employment of the corrugated outer tube 22' enables the bending resistance thereof to be further reduced.

Figure 8:
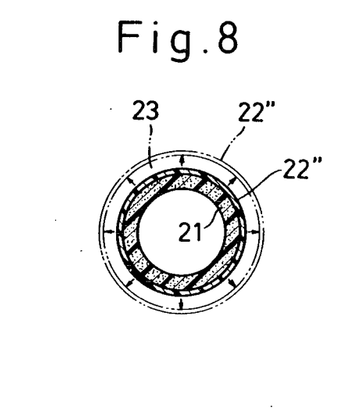
FIG. 8 is a view similar to FIG. 2, but showing another modification of the outer tube.

Moreover, as shown in FIG. 8, an outer tube 22" formed of a thin wall rubber may be substituted for the outer tube 22 in each of the above-described embodiments. The outer tube 22" is normally in intimate contact with the outer peripheral surface of the inner tube 21. When fluid such as, for example, disinfecting fluid is forcibly supplied to the annular region between the inner and outer tubes 21 and 22", the outer tube 22" is inflated, as indicated by the two-dot-and-dash-lines, to form the annular fluid passage 23 between the inner and outer tubes 21 and 22", so that the fluid can flow through the fluid passage 23. In this manner, the fluid passage 23 between the inner and outer tubes 21 and 22" may be formed only when the fluid is caused to flow.

What is claimed is:

1. An endoscope comprising:
    a proximal structure including at least an operating body and provided with at least one proximal opening;
    an elongated inserting structure extending from said operating body and having a distal end provided with at least one distal opening;
    a guide tube assembly extending through said inserting structure and comprising an inner tube formed of porous resin and having one end thereof communicating with said proximal opening and the other end communicating with said distal opening and an outer tube formed of imperforate resin and surrounding said inner tube, said inner tube having a hollow portion communicating with an annular region between said inner and outer tubes through pores of a peripheral wall of said inner tube; and port means provided in at least one of said proximal structure and said distal end of said inserting structure, a fluid being capable of passing through said port means, said port means communicating with said annular region between said inner and outer tubes.

2. An endoscope as defined in claim 1, wherein said porous resin is polytetrafluoroethylene.

3. An endosope as defined in claim 1, comprising flow passageway means including the hollow portion of said inner tube and an annular space formed between said inner and outer tubes, the hollow portion of said inner tube communicating with said annular space through the pores of the peripheral wall of said inner tube.

4. An endoscope as defined in claim 3, wherein said proximal opening is provided in said operating body.

5. An endoscope as defined in claim 3, wherein said port means is provided in said operating body.

6. An endoscope as defined in claim 3, wherein said port means is provided in said distal end of said inserting structure.

7. An endoscope as defined in claim 3, wherein said port means comprises a first port provided in said operating body and a second port provided in said distal end of said inserting structure.

8. An endoscope as defined in claim 3, wherein said proximal structure includes a connector connected to said operating body, said proximal opening being provided in said connector, and tube means for connecting said proximal opening to the hollow portion of said inner tube.

9. An endoscope as defined in claim 8, wherein said port means is provided in said operating body.

10. An endoscope as defined in claim 3, wherein said proximal structure includes a connector connected to said operating body, said port means being provided in said connector, and tube means for connecting said port means to said annular space between said inner and outer tubes.

11. An endoscope as defined in claim 10, wherein said port means comprises a first port provided in said connector and a second port provided in said distal end of said inserting structure.

12. An endoscope as defined in claim 11, wherein said distal end of said inserting structure is provided with a viewing window and a nozzle directed toward said viewing window, said nozzle serving as said second port.

13. An endoscope as defined in claim 3, wherein said flow passageway means has one end communicating with said port means and the other end communicating with at least one of said proximal and distal openings, said fluid including a disinfecting fluid and being supplied from said port means, caused to flow through said flow passageway means and discharged from at least one of said proximal and distal openings.

14. An endoscope as defined in claim 3, including means associated with one of said proximal and distal openings for closing the same, said flow passageway means having one end communicating with the other of said proximal and distal openings and the other end communicating with said port means, said fluid including a disinfecting fluid and being supplied from said other of said proximal and distal openings, caused to flow through said flow passageway means and discharged from said port means.

15. An endoscope as defined in claim 3, wherein said port means comprises a first port provided in said proximal structure and a second port provided in said distal end of said inserting structure, and wherein said endoscope includes means associated with one of said proximal and distal openings for closing the same, said fluid passageway means having one end thereof communicating with the other of said proximal and distal openings and the other end communicating with at least one of said first and second ports, said fluid including a disinfecting fluid and being supplied from said other of said proximal and distal openings, caused to flow through said flow passageway means and discharged from said at least one of said first and second ports.

16. An endoscope as defined in claim 3, wherein said port means comprises a first port provided in said proximal structure and a second port provided in said distal end of said inserting structure, and wherein said endoscope includes means associated with one of said first and second ports for closing the same, said fluid passageway means having one end thereof communicating with the other of said first and second ports and the other end communicating with at least one of said proximal and distal openings, said fluid including a disinfecting fluid and being supplied from said other of said first and second ports, caused to flow through said flow passageway means and discharged from at least one of said proximal and distal openings.

17. An endoscope as defined in claim 1, including:
first attaching means removably associated with said proximal opening for attaching said one end of said inner tube to said proximal opening; and
second attaching means removably associated with said distal opening for attaching said other end of said inner tube to said distal opening.

18. An endoscope as defined in claim 17, wherein said one end of said inner tube is connected to said first attaching means, and said other end of said inner tube is connected to said second attaching means.

19. An endoscope as defined in claim 17, wherein said one end of said inner tube is connected to said first attaching means, and said second attaching means is separable from said other end of said inner tube, said second attaching means cooperating with said distal opening to clamp said other end of said inner tube between a wall surface of said distal opening and said second attaching means.

20. An endoscope as defined in claim 17, wherein said first attaching means is fitted in said proximal opening, and said second attaching means is threadedly engaged with said distal opening.

21. An endoscope as defined in claim 17, wherein said first attaching means has a through bore communicating with one of the hollow portion of said inner tube, and said second attaching means has a through bore communicating with the other end of said hollow portion of said inner tube.

22. An endoscope as defined in claim 1, wherein said outer tube is corrugated.

23. An endoscope as defined in claim 1, wherein said outer tube is formed of thin wall rubber and is in intimate contact with an outer peripheral surface of said inner tube, said outer tube being capable of being inflated when said fluid is supplied to said annular region between said inner and outer tubes, to form an annular space therebetween.

24. An endoscope as defined in claim 1, wherein said inner and outer tubes are maintained out of contact with each other.

* * * * *